(12) United States Patent
Smith et al.

(10) Patent No.: US 7,722,503 B1
(45) Date of Patent: May 25, 2010

(54) SYSTEM AND METHOD FOR AUTOMATING AN EXERCISE ROUTINE

(75) Inventors: Denton D. Smith, Tulsa, OK (US); Lawrence L. Born, Tulsa, OK (US)

(73) Assignee: Scifit Systems, Inc., Tulsa, OK (US)

( * ) Notice: Subject to any disclaimer, the term of this patent is extended or adjusted under 35 U.S.C. 154(b) by 1253 days.

(21) Appl. No.: 11/111,061

(22) Filed: Apr. 21, 2005

Related U.S. Application Data

(60) Provisional application No. 60/564,265, filed on Apr. 21, 2004.

(51) Int. Cl.
*A63B 71/00* (2006.01)
(52) U.S. Cl. .............. 482/8; 482/1; 482/9; 482/900
(58) Field of Classification Search ............ 482/1–9, 482/900–902; 434/247
See application file for complete search history.

(56) References Cited

U.S. PATENT DOCUMENTS

| 5,916,063 | A |   | 6/1999 | Alessandri |  |
|---|---|---|---|---|---|
| 5,931,763 | A |   | 8/1999 | Alessandri |  |
| 5,944,633 | A | * | 8/1999 | Wittrock | 482/4 |
| 6,142,910 | A | * | 11/2000 | Heuvelman | 482/4 |
| 6,397,151 | B1 | * | 5/2002 | Yamagishi et al. | 702/41 |
| 6,561,951 | B2 | * | 5/2003 | Cannon et al. | 482/1 |
| 7,056,265 | B1 | * | 6/2006 | Shea | 482/8 |
| 7,128,693 | B2 | * | 10/2006 | Brown et al. | 482/8 |
| 2002/0055419 | A1 | * | 5/2002 | Hinnebusch | 482/8 |
| 2002/0082142 | A1 | * | 6/2002 | Cannon et al. | 482/1 |
| 2004/0229729 | A1 | * | 11/2004 | Albert et al. | 482/8 |

* cited by examiner

*Primary Examiner*—Glenn Richman
(74) *Attorney, Agent, or Firm*—Fellers, Snider, Blankenship, Bailey & Tippens, P.C.

(57) ABSTRACT

In accordance with a preferred embodiment, there is provided a system and method for assisting a user complete an exercise program. According to a first aspect, there is provided a system that allows a coach to design an exercise program for an individual client and have that program written to portable non-volatile media that is provided to the client. The client then moves from machine to machine during his or her workout program, in each case first inserting the memory card into the selected machine before starting to exercise. The selected machine, if it is one that has been specified in the client's exercise program, will automatically set its performance parameters to match those on the memory card after which the client will be able to immediately start exercising. Optionally, actual performance data from the user's workout will be written back to the memory card for subsequent printing and/or analysis.

20 Claims, 3 Drawing Sheets

SYSTEM AND METHOD FOR AUTOMATING AN EXERCISE ROUTINE

RELATED APPLICATIONS

This application claims the benefit of U.S. Provisional Patent Application Ser. No. 60/564,265 filed on Apr. 21, 2004 and incorporates said application by reference into this disclosure as if fully set out at this point.

FIELD OF THE INVENTION

The present invention relates generally to field of health and fitness and, more particularly, to apparatus and methods for use in assisting a user in selecting and monitoring a workout regimen.

BACKGROUND OF THE INVENTION

The multifold benefits of physical exercise are well established. However, most users are pressed for time and seek to maximize the benefit of such time as they have. Hence, the popularity of a workout regimen that utilizes multiple exercise machines or stations, each of which might provide an exercise that focuses on a particular muscle or muscle group, or that provides cardio (versus strength) training. Further, modern exercise equipment is typically capable of adjustment to accommodate different fitness levels, i.e., a difficulty setting is usually provided that can increase or decrease the amount of exertion that it takes to operate the machine, thereby making it possible for a single machine to accommodate users over a wide range of ability levels.

Coaches, personal trainers, etc., often desire that the clients who are under their care and advisement follow a predetermined sequence of exercises. This might be for many reasons, but among these reasons are a desire to help a client improve in a particular area, to assist a client in reaching a particular fitness goal, or just to prescribe a general fitness protocol or program. Additionally, in most health-clubs and fitness centers, this set of exercises will typically involve multiple exercise machines and varied difficulty level settings on each machine.

However, and as might be expected, it can be difficult for a busy user to keep track of the coach's recommended workout program and to track his or her own performance while following that plan. The prescribed plan could involve four or more different exercise machines, each of which might be operated at a different difficulty level for a different period of time. It would be predictably difficult to commit a complex exercise program to memory and the conventional alternative, e.g., carrying around a printed (or e-mailed) summary of the workout schedule, has obvious disadvantages. Further, many exercise machines provide the user with real-time and/or summary performance statistics (e.g., steps per minute, calories burned, watts generated, etc.) and the user and/or coach may wish to review these statistics in order to gauge the user's progress on the plan. Of course, the user is not likely to be able to remember the performance statistics on even one exercise machine after a few minutes, much less remember the statistics from four or more. Thus, information that might be important to the user's training is typically lost.

Another problem that arises with complex workouts—or even simple workout plans for that matter—is that when the user initially reaches the next machine in the series it likely will have different parameter settings (e.g., exercise duration, difficulty level, etc.) than have been specified for that particular user. This is a well-known inconvenience that is common where exercise machines are utilized by multiple users.

Accordingly, it should now be recognized, as was recognized by the present inventors, that there exists, and has existed for some time, a very real need for a device that would address and solve the above-described problems.

However, before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a preferred embodiment of the instant invention, there is provided a system and method for assisting a user to complete an exercise program. According to a first aspect of the instant invention, there is provided a system that allows a coach, personal trainer, etc., to determine a personal exercise regimen for a client, enter that regimen into a computer program running on a personal computer, and subsequently have that regimen written to a non-volatile memory chip (or similar storage device) through a standard USB port or other computer interface. As should be clear to those of ordinary skill in the art, such a program might include exercises of a specific duration and at a specific difficulty level that are to be performed on a specific piece of equipment. Written on the memory chip key is a representation of the specified workout plan, the intention being that the user for whom the plan was specified will be able to disengage the memory chip/key from the computer and carry it with him or her as he or she moves from machine to machine in the exercise center.

As a next preferred aspect of the instant invention, there is provided an exercise machine that includes a reader that is adapted to read a non-volatile memory card or other storage device (to include portable computing devices that contain such as PDAs) containing an exercise program and respond to the information stored therein. In more particular, in a preferred arrangement, software that is resident within the exercise machine will sense the insertion of the memory card and read at least a portion of its contents into memory. From the information that is read a determination will be made as to whether or not the selected exercise machine has been indicated as part of the user's exercise program and/or whether or not the instant machine is compatible with one or more of the exercises that are stored on the user's memory card. If so, the resident software will read the parameters related to the user's exercise program as it relates to the chosen machine and set the machine's operating parameters to match those specified by the coach. That is, upon recognition that the chosen machine is part of the user's regimen, the previously specified exercise parameters are automatically set for the user on the currently chosen machine, thus sparing him or her the inconvenience of making these settings. However, on the other hand if the user has inserted the memory chip/storage device into an exercise machine that is not a part of his or her program, an error message of some sort will preferably be displayed so that the user will understand that exercise on this machine has not been mandated. The exercise machine's display could be used to communicate this fact or, alternatively, an audio alarm could be generated.

As a next preferred aspect of the instant invention, the client will begin to exercise as prescribed and, at the termination of this phase of the exercise program the machine will write back onto the client's key the measured parameters of the workout including, by way of example only, the actual amount of time exercised, the actual difficulty level employed, the number of calories burned, an average/maximum RPM or similar machine statistics, and, if the proper peripheral equipment is in place, the client's average/maximum heart rate, etc. Additionally, in some preferred embodiments the information that is written will not overwrite the previously stored data, thereby allowing an exercise history profile to be created within the memory key. In other preferred variations, the current exercise data will be written to the memory key and, if there is insufficient space remaining on the key, the most recent exercise data will overwrite the oldest data that was previously stored therein.

Of course, it is anticipated that after completion of the current exercise, the client will proceed to the remaining exercises/machines, in each case inserting the storage device that contains his or her exercise program into the chosen machine before beginning to exercise. Each machine will then preferably read information related to the user's exercise program and, at the conclusion of the client's exercise period on that machine, write some amount of data back to the memory key, the written data containing some measure of the user's performance on the current machine.

As still another preferred aspect of the instant invention, after the exercise is completed the user will take the memory key back to a personal computer or other computing device and place it into electronic communication with its CPU. Then, at least a portion of the user's identifying information, the previously stored exercise program, and any performance data written by an exercise machine will preferably be read. In the preferred arrangement, a summary of the information collected during the previous exercise session will be printed to hard copy or to the computer screen. Alternatively, and preferably in some cases, the report will be e-mailed to the client, if the client's e-mail address is known. Additionally, historical performance values might also be read and printed, if a history is maintained within the key or elsewhere. Preferably, any historical performance data that is read from the key (to include, without limitation, data accumulated during the most recent exercise session) will be written to long-term storage (e.g., hard disk) for later retrieval and review by the user or the coach. Preferably, this information will be stored in database records associated with a particular user so that, if desired, a long-term profile of the user's performance may be compiled and analyzed.

Finally, and as still another preferred aspect of the instant invention, there is provided a system and method for updating the firmware of an exercise machine. More particularly, in one preferred embodiment a system software patch will be written to a non-volatile memory device, such as the memory key discussed previously. Then, after such a device is inserted into the exercise machine, the onboard firmware will read the memory chip, determine that it contains a software patch (rather than a user's exercise profile information) and the load and install the patch. Preferably, this invention is especially suitable for exercise machines that generate their own electrical power and, as such, the patch will not be recognized and loaded until the machine is activated by exercise.

The foregoing has outlined in broad terms the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, the disclosure that follows is intended to be pertinent to all alternatives, modifications and equivalents as may be included within the spirit and scope of the invention as defined by the appended claims. Finally, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which.

DETAILED DESCRIPTION OF THE INVENTION

Turning first to FIGS. 1, 2, 5, and 6, wherein a preferred hardware aspect of the instant invention is illustrated, according to a preferred embodiment there is provided a system and method for creating an exercise profile, writing that profile to portable storage medium, taking the storage medium containing the profile to at least one exercise machine, causing the exercise machine to read the stored exercise profile, setting the exercise machine's performance parameters according to those specified within the stored profile, and, at the end of the exercise period on that machine, recording some aspect of the client's actual performance on the portable storage medium.

In more particular, in the preferred embodiment a coach, personal trainer, etc., will establish a training schedule/template for a particular user. That training schedule will preferably be entered into computer 110 that is running software that has been specifically designed for this purpose. Note that the computer might be a conventional desktop or lap top model (FIG. 5), or it might be a handheld or other smaller CPU (e.g., a PDA running the Palm® operating system or Windows CEO). The only requirement of the computer 110 is that it be in some sense a programmable device and that it be suitable for controlling the reading and writing of information to the memory card 120 or other portable storage device.

Figure 1:
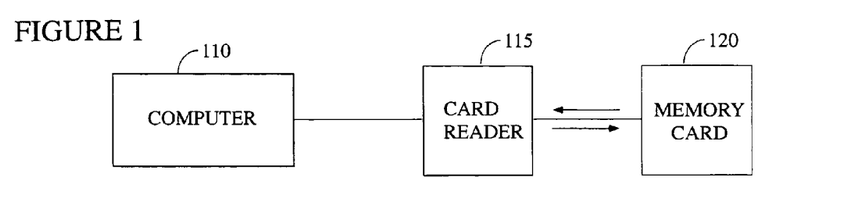
FIG. 1 illustrates generally the preferred hardware components of one aspect of the instant invention.

In communication with the computer program and accessible thereby is preferably a card reader 115 that is designed to accept information from the computer 110 and store it on a removable memory card 120. The card reader 115 should also be able to read information from the memory card 120 and transmit such information back to the CPU of the computer 110 as required. Those of ordinary skill in the art will recognize that there are many card reader-type devices that would satisfy these simple requirements and that the card reader's 115 configuration will ultimately depend on the nature of the memory card 120 that is chosen.

Finally, memory card 120 is preferably a non-volatile memory card such as are common in the industry. For example, memory card 120 might be a compact flash-type card, a memory stick, a pen drive, a secure digital card, or some other memory device. Further, in some preferred arrangements it will be a custom-designed memory chip and especially one that is ruggedized for use in the environment of a health club or gym where exposure to moisture is a possibility. That being said, those of ordinary skill in the art will recognize that any portable storage media including, without limitation, a magnetic disk, an optical disk, a magneto-optical disk, flash RAM, a CDRW disk, etc., could be used depending on the circumstances, the only requirement being that the device 120, what ever its form, must be able to receive and store at least identifying information pertaining to the client therein. Of course, the reader 220 will need to be compatible with whatever media type is written via the card writer 115.

Because of the environment in which the instant invention is preferably used, there is an obvious concern about exposure of the memory card 120 to moisture, dirt, etc., any of which might potentially corrupt the information written therein. As a consequence, it is preferred that during the process of writing to and reading from the card 120 that some form of error checking be implemented either on a record level or in connection within individual items that are written to the card 120. For example, a simple check sum might be calculated and stored on the card 120, a cyclic redundancy checksum (e.g, CRC-16, or CRC-32) might be calculated, or some other procedure could be implemented to help insure data integrity.

Figure 2:
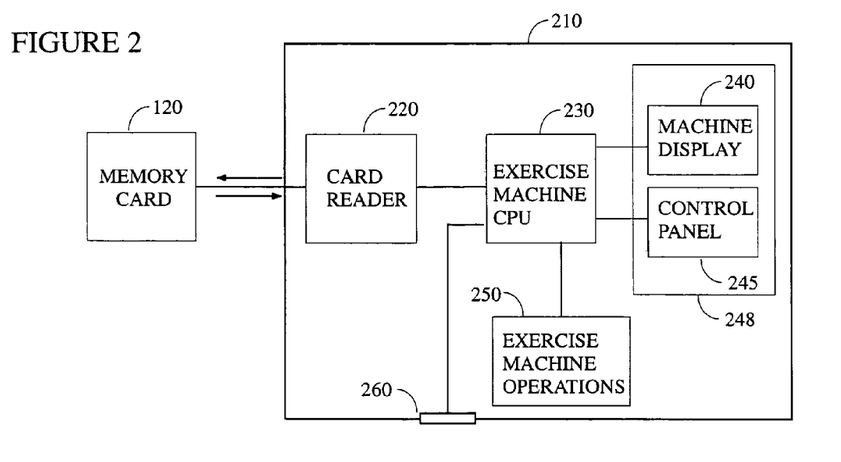
FIG. 2 contains an illustration of a preferred configuration of an exercise machine that would be suitable for use with the instant invention.

As is indicated in FIG. 2, the memory card 120 will be removed from the card reader 115 after the exercise program is written thereto and taken by a user to an exercise machine 210 and placed in communication with a card reader 220. Note that the card reader 220 might be either integral to the exercise machine 210 or in communication therewith. This machine 210 might be any conventional or unconventional exercise machine including, without limitation, a treadmill, a recumbent bike, an upright bike, an upper-body crank, a recumbent stepper, an upright stepper, an elliptical exercise machine, a climber, etc. All that is required is that it contains at least one operating parameter (e.g., duration, difficulty level, incline, etc.) that can be automatically modified under software control to adjust the user's workout intensity level.

Preferably internal to the exercise machine 210 (or, alternatively, external to the machine 210 but in electronic communication with it) is a card reader 220 that is compatible with the memory card 120. That is, the only requirement is that the card reader 220 be able to read information from the memory card 120 and preferably, as described below, also able to write information to it under control of a CPU 230 which, again, might be internal to the exercise machine or in electronic communication with it.

Preferably the CPU 230 will also be in electronic communication with the exercise machine front panel, which would typically include the display 240 and/or any manually activated switches that a user can use to control the machine operations (e.g., control panel 245), but this is not an absolute requirement. It is certainly possible that the front panel operations might be managed by a separate CPU, although that is not preferred. Note that in the preferred arrangement machine display 240 is used to communicate information to the user relating to the workout template that is resident within the user's memory card 120 and the control panel 245 will preferably be readable by the CPU 230 for purposes of receiving information from the user for that same purpose. Collectively, the display 240 and control panel 245 comprise the user interface 248 portion of the exercise machine 210.

CPU 230 necessarily must be in electronic communication with and able to control at least some of the operations of the exercise machine 210. By operations is meant such things as timers, effort level, etc. Those of ordinary skill in the art will recognize that the precise nature of the operations that could potentially be controlled from CPU 230 will depend on the particular exercise machine. As is explained more fully below, one of the main functions of software that runs within the CPU 230 is to set machine parameters according to data that is preferably found stored on and read from the memory card 120.

Finally, an optional but preferred function of the CPU 230 is to monitor the client's performance. Such performance might include parameters related to the machine's operations (e.g., max RPM) that might be collected by internal machine sensors or information that is related more personally to the client. For example, port 260 might be configured to read biometric information such as the client's pulse rate via a USB, RS 232, RJ45, etc., connector. Similarly, port 260 could be receiver that collects biometric information wirelessly. Such performance information—whether machine or client in origin—will preferably be written at the conclusion of the exercise routine back to the memory card 120 for subsequent analysis, preferably by a separate computer program. This aspect of the instant invention will be discussed in greater detail below.

Figure 3:
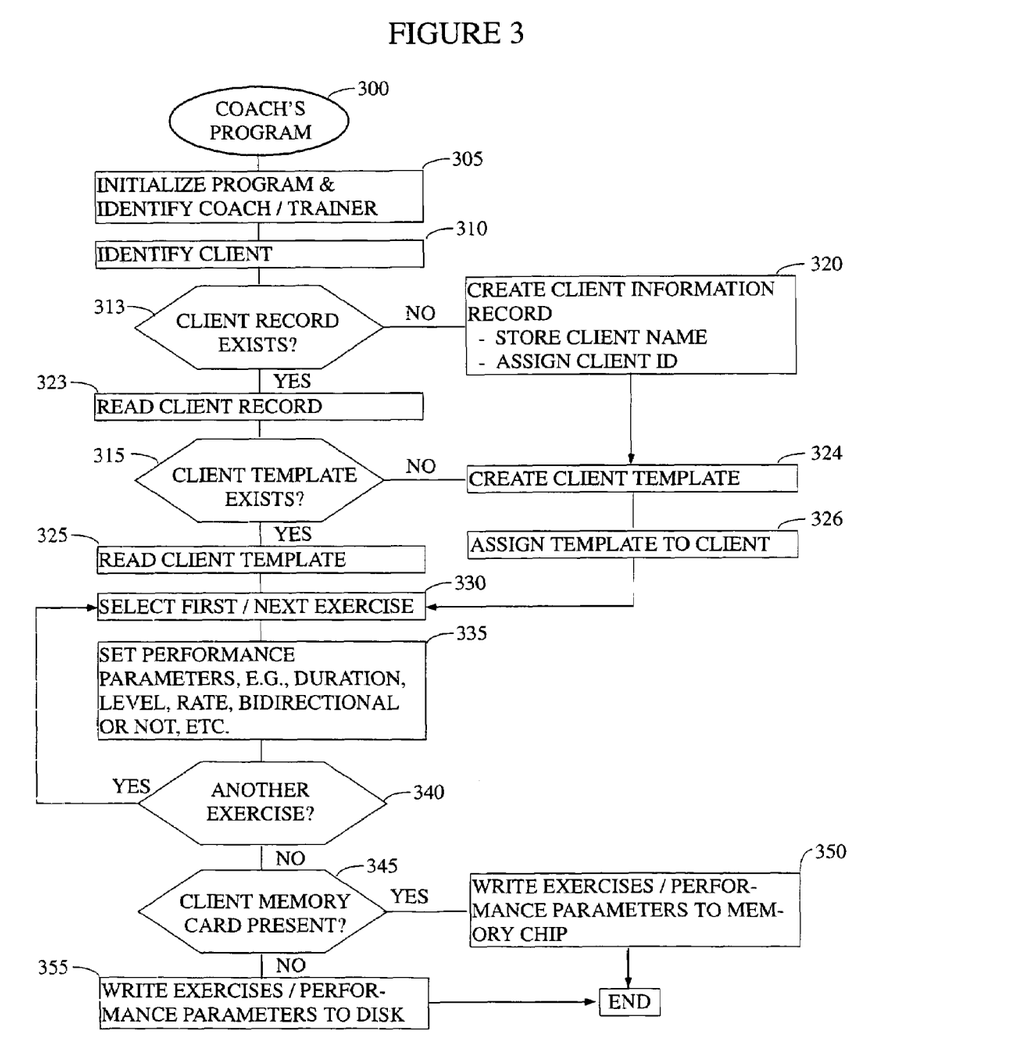
FIG. 3 contains a flowchart that illustrates some preferred steps in the program that assists in the creation and storage of an exercise program.

Turning next to FIG. 3, there is provided in this figure a preferred general flow diagram for the computer program 300 that is utilized by the coach/trainer. In conjunction with this figure, it should be noted and remembered that in the preferred embodiment the instant inventors prefer that the specified exercise regimen be comprised of a circuit training system that utilizes several different machines, each of which is preferably capable of bi-directional resistance. Additionally, and in the preferred embodiment, the client will be required to exercise an equal amount of time on each machine, i.e., the duration parameter will be set to the same value for each machine in the exercise program. Although this might be done for many reasons, one prominent rationale for keeping the time spent on each machine about the same is that it promotes traffic flow within the exercise facility. That is, in a gym where multiple users are following similar exercise schedules, a user that monopolizes a one-of-a-kind machine (or one of a few in larger gyms) for an excessive period of time can create a bottleneck that prevents others from completing their own programs. Thus, by specifying that an equal amount of time be spent on each machine, the coach will tend to be, to the extent possible, optimizing use of the available equipment. Finally, although the equal-time requirement might be enforced in many ways, in some preferred embodiments all of the resistances, inclines, weights, etc., of an exercise machine could be set to their minimum values (e.g., "zero") at the end of the prescribed time period. Thus, a user would have little incentive to stay on a machine beyond the coach-specified exercise duration.

The exercise plan will preferably consist of machines that can provide at least three of the following activities: walk, pedal, push, and pull. At least one of the machines will preferably be capable of an upper body strength and cardio mode and one machine should be capable of a lower body strength and cardio mode.

Continuing with the discussion of the coach program, as an initial preferred step, the coach or trainer will activate the program and allow it to initialize its program variables as is commonly done (step 305). Additionally, it is preferred that the coach identify himself or herself to the program, such identification being used, for example, for security purposes, to restore a previously customized environment, etc.

As a next preferred step the client is identified (step 310) and, if a client record exists, it will preferably be read (steps 313 and 323), whereas if a client record cannot be found, the instant program preferably creates one (step 320) using information provide by the coach or trainer. As a next preferred step, a determination will be made as to whether or not an exercise template has been set up for this client (step 315). If so, it will be read from disk or other nonvolatile storage (step 325). Alternatively, a template will be generated for this client (step 324) and assigned to him or her (step 326). If a profile for this client has been created and stored previously, that profile will be read (steps 315 and 325). Otherwise, the trainer will optionally be given the opportunity to create such a profile by identifying the client, receiving (or specifying) a client identification code, etc. (steps 315 and 320).

In either case, the program preferably next enters a loop or other section of programming code that allows the coach or trainer to specify a series of exercises and performance levels (steps 330 through 340). Preferably, the coach will be prompted to select from among a plurality of exercise machines and/or exercise types (step 330). Next, the coach will be asked to set performance levels for this particular client (step 335), wherein such performance levels could include exercise duration, difficulty level, performance rate, bi-directional (or not), inclination (e.g., in the case of a treadmill), interval training (or not), etc. In some cases, the coach might also specify whether the user will be allowed to modify the coach's choices or not. Of course, those of ordinary skill in the art will recognize that the particular performance parameters that are available to the coach will generally be a function of the particular type of equipment that has been selected.

That being said, in the preferred embodiment the coach will specify an exercise regimen that includes both aerobic and anaerobic (strength) machines as part of the workout. Further, preferably the workout will include interval training of some sort (e.g., where the machine load is engaged for some short period of time and then disengaged for another period of time). Additionally and preferably, one or more of the exercise machines will utilize rotary motion.

The previous process will continue with selection of another machine/exercise until the coach has completed the creation of the client's exercise profile (i.e., until the "NO" branch of step 340 is reached). Then, if the user's memory chip is present in the card reader 115 ("YES" branch of decision step 345), the exercise template will preferably be written thereto (step 350). The writing of the template will preferably include such information as the user's identification, together with the exercise series and the performance parameters (the template) which have been selected by the coach. Table 1 contains a listing of the sorts of information that might be stored in the memory card as part of the template. Note that, as is indicated in the following table, it is specifically contemplated that multiple templates might be stored on a single memory card.

TABLE 1

Example Memory Card Contents

| Parameter | Meaning |
| --- | --- |
| Key Size | Value in bytes. |
| KeyID | 32 bit value used to identify the key |
| Client's Name | Clients Name |
| Units (American or Metric) | Units stored on key |
| Beginning of Template Area | Pointer to beginning of the template area. |
| Templates on key | Number of templates on this key |
| Beginning of Session Area | Pointer to beginning of the session area. |
| Sessions On Key | The total number of sessions on the key. |
| Steps Left | Number of steps left in this template (Pointer to start of template points here) |
| Equipment Mode | The mode the equipment is set to for this step of the template |
| Equipment Type | Type of equipment this step is for |
| Step Identifier | The type of step this is ie Upper body cardio, lower body strength. |
| Mode Val 1 | The target value for this mode |
| Mode Val 2 | Second target value for this mode |
| Mode Val 3 | 3rd target value for this mode |
| Duration | Number of seconds for segment |
| Complete | Indicates that this step has been completed |
| Steps Left | Number of steps left in this template (Pointer to start of template points here) |
| Equipment Type | Type of equipment this step is for |
| Equipment Mode | The mode the equipment is set to for this step of the template |
| Step Identifier | This type of step this is ie Upper body cardio, lower body strength. |
| Mode Val 1 | First target value for this mode |
| Mode Val 2 | Second target value for this mode |
| Mode Val 3 | Third target value for this mode |
| Duration | Number of seconds for segment Example = 5 minutes (300 secs) |
| Complete | Indicates that this step has been completed |
| Session Flags | Flags for various session options (Pointer to start of sessions points here) |
| Equipment Type | Type of equipment that was used for this exercise session [the pointer in header points to here] |
| Equipment Mode | Mode setting for the equipment. |
| Profile selected | If this session has a profile associated with it then this indicates which profile. Zero indicates no profile. |
| Template Index | Indicates which step in the template this session is related to |
| Actual duration (seconds) | Actual time the user worked out in seconds Example = 5 minutes (300 secs) |
| avg value of RPM or speed | Average RPM or speed in treadmill. Value in RPM or 1/10 of an MPH Example = 4.7 mph |
| max value for RPM or speed | Maximum RPM or speed if treadmill. Value in RPM or 1/10 of an MPH Example = 6.2 mph |
| max value for Elevation | Max elevation if treadmill. Percent Grade 1/10 Example = 12% |
| avg value for Elevation | Average elevation if treadmill. Percent grade 1/10 Example = 8% |
| avg value for heart rate | Average heart rate for workout for user during workout. Example = 128 bpm |
| max value for heart rate | Maximum heart rate attained by user during workout. Example = 149 bpm |
| Ave Wattage | Average wattage reading |
| Max Wattage | Maximum wattage reading |
| Distance | Total distance traveled in 1/100 of a mile. Example = 2.84 miles |
| Distance Vertical | Treadmill and Climbers - total vertical distance traveled Value in 1/10 feet |
| Max level or intensity | |
| Average level or intensity | |
| Last level or intensity | |
| Equipment Firmware Version | Major, Minor, Release |
| Session Flags | Flags for various session options |
| Equipment Type | Type of equipment that was used for this |

TABLE 1-continued

Example Memory Card Contents

| Parameter | Meaning |
|---|---|
| | exercise session |
| Equipment Mode | Mode setting for the equipment. |
| Profile selected | If this session has a profile associated with it then this indicates which profile. Zero indicates no profile. |
| Template Index | Indicates which step in the template this session is related to |
| Actual duration (seconds) | Actual time the user worked out in seconds<br>Example = 5 minutes (300 secs) |
| avg value of RPM or speed | Average RPM or speed in treadmill. Value in RPM or 1/10 of an MPH<br>Example = 4.7 mph |
| max value for RPM or speed | Maximum RPM or speed if treadmill. Value in RPM or 1/10 of an MPH<br>Example = 6.2 mph |
| max value for Elevation | Max elevation if treadmill. Percent Grade 1/10<br>Example = 12% |
| avg value for Elevation | Average elevation if treadmill. Percent grade 1/10<br>Example = 8% |
| avg value for heart rate | Average heart rate for workout for user during workout. Example = 128 bpm |
| max value for heart rate | Maximum heart rate attained by user during workout. Example = 149 bpm |
| Max Wattage | Maximum wattage reading |
| Ave Wattage | Average wattage reading |
| Distance Vertical | Treadmill and Climbers - total vertical distance traveled Value in 1/10 feet |
| Distance Horizontal | Total distance traveled in 1/100 of a mile. Example = 2.84 miles |
| Average level or intensity | |
| Max level or intensity | |
| Last level or intensity | |
| Equipment Firmware Version | |

Note further that the parameters listed in Table 1 are merely examples of the sort of information that might be stored there and those of ordinary skill in the art will be able to suggest many other parameters that could additionally, or alternatively, be stored on a memory card or other portable storage device of the sort utilized herein. For example, messages of different sorts might be stored on the card including, for example, messages that welcome the user to the machine, messages that direct the user to move to the next machine, messages that instruct the user to reverse directions (in the case that the machine supports bi-directional exercise), custom messages from the coach, etc.

Returning to the discussion of FIG. 3, in the event that the client's memory card is not currently in the reader 115, the information that has just been entered will preferably be saved to disk or other non-volatile storage (step 355) to await the insertion of a matching card into the card reader 115, at which time the information will preferably automatically be written thereto.

Figure 4:
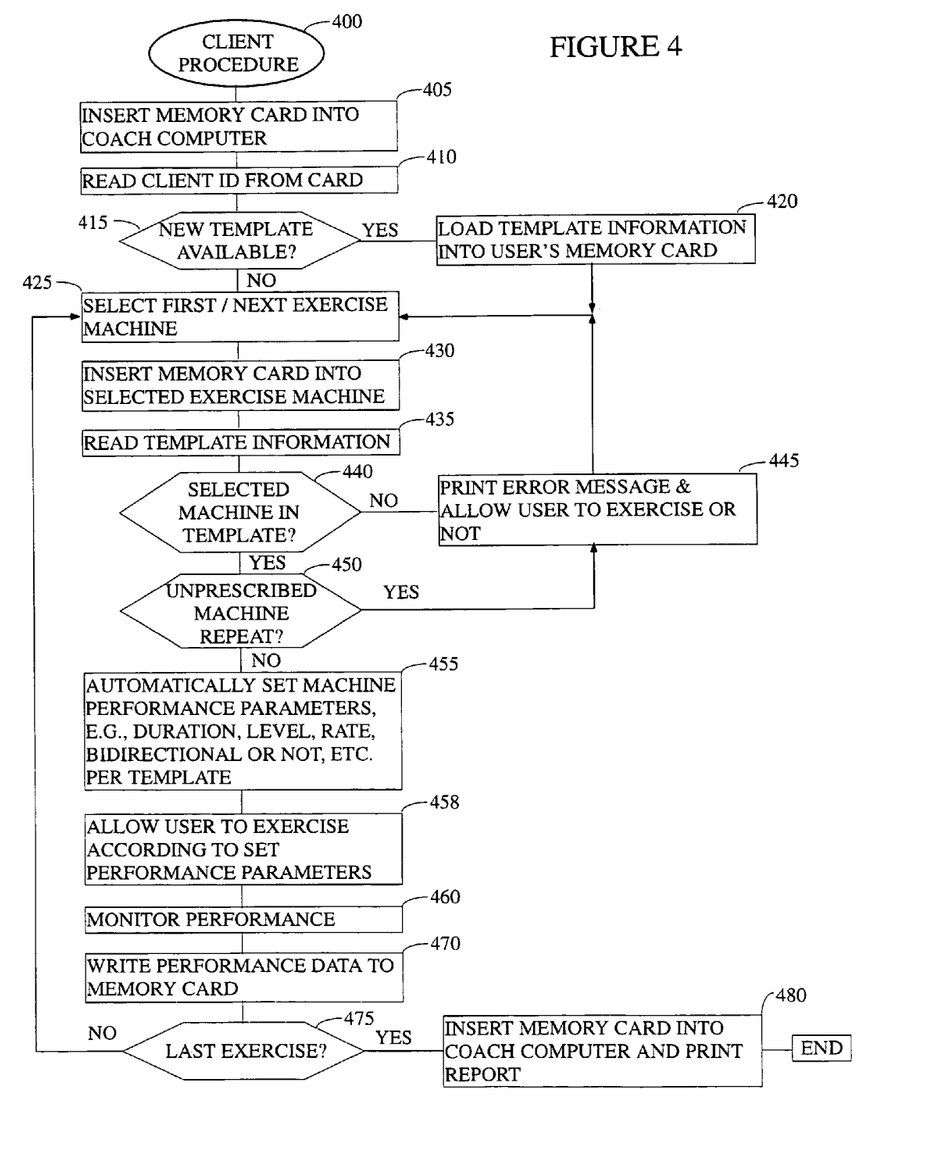
FIG. 4 illustrates a preferred operating logic of the instant invention from the standpoint of a client.
Figure 5:
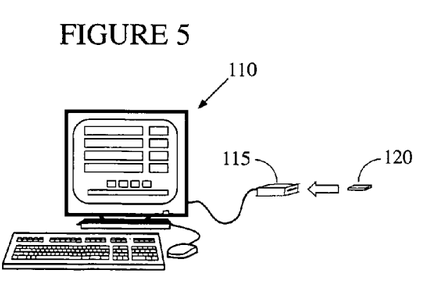
FIG. 5 contains an illustration of a preferred hardware configuration for use by the coach.
Figure 6:
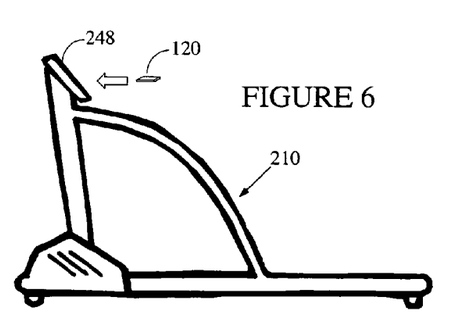
FIG. 6 illustrates a preferred hardware configuration for use by the client.

Turning next to FIG. 4 wherein a preferred logic of the client aspect 400 of the instant invention is illustrated, there is provided a method for executing a predetermined series of exercises under computer control. As a first preferred step 405, the client will insert his or her memory card into a computer that has access to the information that was entered previously on the client's behalf by the coach (step 405). Note, of course, that this need not be the same physical computer used by the coach but could instead be a separate computer that is networked to the one utilized by the coach/trainer. Further, this step will not be necessary in those cases where the client has a workout plan that was stored previously and all that is desired is to repeat that same exercise program.

Assuming that the client has elected to synchronize his or her memory card 120 with the coach's computer, a next preferred step is to read the client ID information from the card and determine whether or not a modified or newer version of the client's template is available (steps 410 and 415). If so, preferably this new information will be loaded into the user's memory card (step 420) for subsequent reading by the exercise machines.

As a next preferred step, the user will carry the memory card 120 that contains the exercise template stored thereon and move to a first exercise machine (step 425). After inserting the card (step 430) into a machine that can read it, the software within the chosen exercise machine (which is preferably resident therein as firmware) will read the template information (step 435).

Among the information that is stored in the template will be some indication of, for example, a specific machine type or identity or, alternatively, an exercise type. That is, in one preferred variation a coach will specify that the client should spend time on a specific named machine in the health club or gym. The client will only be able to complete that portion of the program when that single machine (or machine of the same type) becomes available. Alternatively and preferably, the coach might have specified a type of exercise (e.g., upper body cardio, lower body strength, etc.) that could potentially be performed on more than one machine (e.g., one of multiple identical stair stepper machines at the current location) or on more than one type of machine. In either case, the software within each exercise machine will preferably be able to recognize at least the type of exercise that has been specified and determine whether such an exercise is possible on that machine.

If, after examining the client's card 120 the software within the exercise machine determines that the client has selected a machine that is incompatible with the coach's prescription, an error, warning, or other message will preferably be printed on the machine's display 240 to indicate to the user that the selected machine cannot perform any of the activities specified within the template (steps 440 and 445). Of course, an audible alarm (as opposed to a printed message) could certainly be used instead of (or in conjunction with) the printed message. In either case, it may be that the user will elect to exercise on the selected machine in spite of the warning and, preferably, the machine will be programmed to allow that to happen, although other arrangements are certainly possible. However, in the event that the client elects to exercise on a wrongly selected machine, in the preferred embodiment any performance data generated on this machine will not be written to the card 120 at the end of the session, although in some circumstances that might be desired.

As a next preferred step 450, the exercise machine software will determine whether or not this is the second time the user has visited this machine during the current exercise period. Unless this revisit has been prescribed by the coach or trainer, the user will be notified of that fact (step 445) and allowed to exercise (or not) depending on the desires of the programmer. Of course, if the coach has required multiple visits to the same machine, the instant machine will simply note that this is the second (or third, etc.) of multiple visits.

As a next preferred step, the on-board software will automatically set the performance parameters of the exercise machine to at least approximately match those specified by the coach (step 455). As examples only of the sorts of parameters that might be set are quantities such as workout duration, exertion level, exercise rate, whether or not the user is to perform the exercise in a bi-directional manner, etc. Those of ordinary skill in the art will readily realize that the sorts of parameters that might be specified and set are limited only by capabilities of the exercise machine and the imagination of the programmer. Of course, it is certainly possible that the selected machine will not be able to exactly match the precise exercise parameter values on the memory card 120 (e.g., if the coach had specified a treadmill incline of 4° and the selected machine only allowed adjustments in 5° increments). In such a case, it is expected that parameter values that are reasonable close to the specified ones will be used instead.

Note that, in some preferred variations, the client will not be allowed to deviate from the exercise schedule that has been stored on the card 120 (i.e., the "key only" mode, hereinafter). That is, in this embodiment the user will not be able to manually vary the parameters that have been set via the memory device 120. So, for example, if the coach specifies a ½ mile session on the treadmill at a 5% incline, the user will not be allowed to manually modify or override those parameter settings. In other embodiments, of course, the user will be allowed to modify one prescribed parameter value (e.g., by changing "½ mile" to "¾" mile) but not another. Whether or not a key only mode will be implemented on a particular exercise machine is a decision that will preferably be left to the discretion of the coach or trainer.

Next, the user will begin to exercise according to the parameter settings specified by the coach (step 458) and/or optionally modified by the user if such modification is permitted. Of course, if the key only mode has been selected by the coach, the user will be required to exercise at the parameter settings stored on the card 120. During such exercise, the instant software will preferably monitor the client's performance on the selected machine (step 460), with the preferred intention of writing information indicative of that performance to the user's memory card 120 at the end of prescribed exercise (step 470). In some preferred variations of the instant invention the performance information will not be written back to the memory card. This might occur if, for example, the client had utilized a "general purpose" or "basic" memory card that had not been personalized to him or her. By way of explanation, in some instances a coach might want to set up generic or standardized exercise schedules that would be followed by multiple clients. In such a case, a client would preferably pickup a card with the appropriate exercise written thereon and then move from machine to machine according to its instructions. In this case, the key would likely not be personalized to the user and, consequently, the exercise machine would not need read user information therefrom but, instead, would read only the exercise schedule.

As has been indicated previously, the user will preferably move from machine to machine, in each case inserting his or her memory card 120 into the machine before beginning to exercise and having the internal machine operating system of the selected machine set its performance parameters to match those of the prescribed workout program (i.e., steps 425 through 475).

Finally, after the client has completed the last exercise in the series (step 475), the client will optionally return to the coach's computer (or another computer that is programmed as described hereinafter) to request and view a summary of the individual's performance data that was collected during the previous (or any earlier stored) exercise session (step 480). Clearly, the present performance could readily be compared in report form with earlier performances that are stored within the client's memory card 120 (if any) or could be compared with historical performance statistics that have been accumulated in a master database that is designed for that purpose, i.e., if a master database were to be provided that read each sessions performance data and stored that information under the client's ID.

Note that the performance summary/report that is produced for the client might be printed on the computer screen, printed in hardcopy form for the client to take with him or her, written to a removable magnetic, optical, or magneto-optical media, and/or sent to the client via e-mail. Of course, printing the report on a computer screen is adequate to give the client a "quick look" at his or her historical data and would be useful in some circumstances, but most clients will likely want to study the report in greater detail than a screen listing would provide. Printing the report to paper for the client to take with him or her provides such an opportunity for further study, but the care of paper items around moisture is problematic. Thus, in the preferred arrangement the report will be e-mailed to the client for review at his or her leisure at home or the office and away from the sorts of contaminants that are common in health clubs, gyms, and the locker rooms of same. Alternatively, the report could be written to a removable storage device (e.g., floppy disk, pen drive, CDR or CDRW disk, etc.), preferably in a standard format (e.g., a Microsoft® Word file or a PDF file) for transportation by the client to a remote viewer/printer.

As still another preferred embodiment of the instant invention, the instant inventors have developed an improved method for updating the firmware on an exercise machine. Heretofore, it has been necessary to swap boards and/or chips within the exercise machine in order to update its internal operating software, a procedure that often requires a visit by a skilled technician. However, the instant inventors have determined that it is possible to utilize the instant system to deliver software updates as follows. A software patch is written to a memory card 120 or other storage device of the same sort described above. Preferably, an indicator flag will be set within that card 120 to indicate that it contains a software patch rather than a client template. Then, the card 120 is sent (e.g., via mail) or carried to the site where the exercise equipment is to be updated. Upon insertion of the memory chip into the interface that has been provided for the purpose (i.e., card reader 220) the software on-board the exercise device will recognize that it has been delivered a software patch and load that patch into the system according to methods well known to those of ordinary skill in the art. Finally, it should be noted that in some instances it might be necessary to begin operating the exercise equipment in order for the patch to be loaded. This might be necessary where, for example, the operating system is powered by current that is generated by the client's exercise efforts (e.g., a stationary bicycle might contain an alternator that generates current to power the display as the client exercises, thereby eliminating the need for the machine to be plugged into the wall).

As still a further preferred embodiment, there is provided an invention substantially as described above but wherein the wherein the user's exercise schedule contains both aerobic and anaerobic exercise types in a single circuit. In more particular, in this preferred variation the coach will create an exercise schedule that contains some combination of aerobic and anaerobic (strength) exercises. As before, the schedule will be written to the memory card 120 by the coach for subsequent use by the user during his or her workout.

Additional Remarks

It should be noted and remember that, although the instant invention preferably utilizes a memory chip or similar device that contains all of the details of the workout schedule and is carried by the user from machine-to-machine during the actual workout, that is not strictly required. In other preferred embodiments, the exercise machines will be connected via a wired or wireless network to a central server. The user merely identifies him or herself to the piece of exercise equipment (e.g., by inserting a non-volatile memory chip, by using a magnetic or other card reader, etc.) and the software within the exercise equipment then contacts the central server to obtain the exercise template. Clearly, the user's performance data, rather than being written back to the memory chip could instead be written back over the network to the central server where it will be maintained for analysis by the coach and/or the client. Of course, in such a case the user's "key" could be non-modifiable, as it would only be read. Those of ordinary skill in the art will recognize that any conventional or unconventional storage medium might potentially be used including, without limitation, CD, DVD, magnetic disk, magnetic tape, magneto-optical disk, RAM, ROM, EPROM, flash RAM, or any other mass storage hardware suitable for holding digital information therein for later recall.

Additionally, it should be noted that portable computing devices (such as Palm® or Microsoft CE®-based handheld systems) contain nonvolatile memory that could be used according to the instant invention. In this scenario, the card reader 115 could take the form of an IR port, a wireless transceiver (e.g., IEEE 802.11b, IEEE 802.11 g, or other wireless LAN), or a direct-connect cradle. In any case, for purposes of the instant invention, the term "memory card" should be construed broadly to include traditional non-volatile storage as has been described previously, as well as a portable computing devices that contain non-volatile memory (to include hard disk drives) therein.

Those of ordinary skill in the art will recognize that there are many active devices that could serve for purposes of the instant invention as the coach's CPU or the CPU of the piece of exercise equipment. More particularly, the instant invention minimally requires that the microprocessor/CPU be an active device, i.e., one that is minimally programmable to achieve the functionality (e.g., reading a client's information from a storage device, determining whether the selected exercise machine is part of the client's program, etc.). Of course, these sorts of modest requirements may be satisfied by any number of programmable logic devices ("PLD") including, without limitation, gate arrays, FPGA's (i.e., field programmable gate arrays), CPLD's (i.e., complex PLD's), EPLD's (i.e., erasable PLD's), SPLD's (i.e., simple PLD's), PAL's (programmable array logic), FPLA's (i.e., field programmable logic array), FPLS (i.e., fuse programmable logic sequencers), GAL (i.e., generic array logic), PLA (i.e., programmable logic array), FPAA (i.e., field programmable analog array), PsoC (i.e., programmable system-on-chip), SoC (i.e., system-on-chip), CsoC (i.e., configurable system-on-chip), ASIC (i.e., application specific integrated chip), etc., as those acronyms and their associated devices are known and used in the art. Further, those of ordinary skill in the art will recognize that many of these sorts of devices contain microprocessors integral thereto. Thus, for purposes of the instant disclosure the terms "processor," "microprocessor" and "CPU" (i.e., central processing unit) should be interpreted to take the broadest possible meaning herein, and such meaning is intended to include any PLD or other programmable device Finally, those of ordinary skill in the art will recognize that it is not uncommon for a single exercise machine to have multiple exercise modalities incorporated therein. For example, a single machine might offer a variety of strength exercises such as curls, presses, and raises, etc. In such an instance, for purposes of the instant disclosure each separate exercise modality will be considered as a different exercise "machine." So, for example, a coach might create an exercise program that requires the user to perform two different exercises on the same apparatus by operating it in different modes. Thus, for purposes of the instant disclosure when a user is said to utilize different "exercise machines" or "exercise apparatuses", those terms should be broadly construed to include both the use of two or more stand-alone single purpose exercise devices, as well as the use of two or more modalities of a multiple-modality exercise device.

Thus, it is apparent that there has been provided, in accordance with the invention, a monitor and method of operation of the monitor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. A method of performing an exercise regimen, comprising the steps of:
   a. defining an exercise schedule for a user, wherein
      said exercise schedule includes exercises on at least two different machines,
      each of said at least two different machines has at least one modifiable exercise parameter associated therewith, and,
      said exercise schedule includes a predetermined parameter value for at least one of said modifiable parameters associated with each of said exercise machines;
   b. storing said exercise schedule on a non-volatile computer-readable medium;
   c. selecting one of said at least two exercise machines;
   d. within said selected machine
      (d1) reading at least a portion of said stored exercise schedule from said non-volatile medium, thereby reading at least one of said predetermined values of said modifiable parameters associated with said selected exercise machine,
      (d2) automatically setting at least one of said selected machine modifiable exercise parameters to a value at least approximately equal to one of said read predetermined values, and,
      (d3) (i) requiring the user to exercise on said selected machine according to at least one of said modifiable exercise parameter values set in step (d2);
         (ii) obtaining an estimate of the user's performance on said selected machine,
         (iii) writing a value representative of said estimate of the user's performance to said non-volatile medium; and,
   e. performing steps (c) through (d) at least twice, each on a different of said at least two exercise machines thereby, causing the user to perform said exercise regimen and storing the values representative of said estimates of the user's performance for each of said at least two exercise machines.

2. A method according to claim 1, wherein said modifiable parameters are selected from a group consisting of an exercise duration, a number of repetitions, a horizontal distance, a vertical distance, a ramp elevation, and a difficulty level.

3. A method according to claim 1, wherein step (b) comprises the step of:
   (b1) storing said exercise schedule on a removable non-volatile memory card.

4. A method according to claim 1, further comprising:
(f) reading any of said written values representative of said estimate of the user's performance from said non-volatile medium; and,
(g) displaying any of said read values for review by the user.

5. A method according to claim 1, wherein said predetermined parameter values comprise an exercise duration on each of said two different machines.

6. A method according to claim 5, wherein said exercise durations on each of said two different machines are all a same duration.

7. A method according to claim 1, wherein step (d3) comprises the steps of:
(i) requiring the user to exercise on said selected machine according to said exercise schedule by prohibiting modification by the user of any of said at least one modifiable exercise parameters set in step (d2).

8. A method according to claim 1, wherein step (d1) comprises the steps of:
(i) identifying the user, and,
(ii) reading at least a portion of said stored exercise schedule from said non-volatile medium, thereby reading at least one of said predetermined values of said modifiable parameters associated with said selected exercise machine.

9. A method according to claim 1, wherein said at least two different machines include a first machine that provides an aerobic workout and a second machine that provides an anaerobic workout.

10. A method according to claim 1, wherein said exercise schedule includes interval training on at least one of said at least two different machines.

11. A method according to claim 1 wherein the exercise regimen is performed at least twice, and wherein values representative of said estimate of the user's performance from each of said at least two respective regimens are written to said non-volatile medium.

12. An exercise machine, comprising:
a. an exercise apparatus, said exercise apparatus having at least one electronically modifiable difficulty parameter;
b. a memory card reader;
c. a microprocessor in electronic communication with said exercise apparatus and said memory card reader, said microprocessor being programmed to at least perform the following steps:
(c1) reading from a memory card via said memory card reader at least a portion of an exercise schedule, wherein said read portion of said exercise schedule comprises at least one predetermined parameter setting for one of said electronically modifiable difficulty parameters,
(c2) automatically modifying at least one of said electronically modifiable difficulty parameters to at least approximately match at least one of said read predetermined parameter settings, and,
(c3) prohibiting modification by a user of at least one of said at least one automatically modified difficulty parameters.

13. An exercise machine according to claim 12, wherein said exercise apparatus is selected from a group consisting of a treadmill, a recumbent bike, an upright bike, an upper-body crank, a recumbent stepper, an upright stepper, an elliptical exercise machine, and a climber.

14. A method according to claim 12, wherein said at least one electronically modifiable difficulty parameters are selected from a group consisting of an exercise duration, a number of repetitions, a horizontal distance, a vertical distance, a ramp elevation, and a difficulty level.

15. An exercise machine according to claim 12, wherein step (c3) comprises the step of:
(i) prohibiting modification by a user of all of said automatically modified difficulty parameters.

16. A method of performing an exercise regimen, comprising the steps of:
a. defining an exercise schedule for a user, wherein
said exercise schedule includes exercises on at least two different machines, each of said at least two different machines has at least one modifiable exercise parameter associated therewith, and,
said exercise schedule includes a predetermined parameter value for at least one of said modifiable parameters associated with each of said exercise machines;
b. storing said exercise schedule on a non-volatile computer-readable medium;
c. selecting one of said at least two exercise machines;
d. within said selected machine
(d1) reading at least a portion of said stored exercise schedule from said non-volatile medium, thereby reading at least one of said predetermined values of said modifiable parameters associated with said selected exercise machine,
(d2) automatically setting at least one of said selected machine modifiable exercise parameters to a value at least approximately equal to one of said read predetermined values, and,
(d3) requiring the user to exercise on said selected machine according to said exercise schedule by prohibiting modification by the user of at least one of said at least one modifiable exercise parameters set in step (d2); and,
c. performing steps (c) through (d) at least twice, thereby causing the user to perform said exercise regimen.

17. A method according to claim 16, wherein step (d3) comprises the steps of:
(i) requiring the user to exercise on said selected machine according to at least one of said modifiable exercise parameter values set in step (d2);
(ii) obtaining an estimate of the user's performance on said selected machine,
(iii) writing a value representative of said estimate of the user's performance to said non-volatile medium.

18. A method according to claim 17, further comprising:
(f) reading any of said written values representative of said estimate of the user's performance from said non-volatile medium; and,
(g) displaying any of said read values for review by the user.

19. A method according to claim 16 wherein the exercise regimen is performed at least twice, and wherein values representative of said estimate of the user's performance from each of said at least two respective regimens are written to said non-volatile medium.

20. An exercise machine according to claim 16, wherein step (d3) comprises the step of:
(i) prohibiting modification by a user of all of said automatically modified difficulty parameters.

* * * * *